United States Patent [19]

Schein

[11] 4,340,596
[45] Jul. 20, 1982

[54] PREPARATIONS FOR THE TREATMENT OF THEILERIOSIS AND THEIR USE

[75] Inventor: Eberhard Schein, Berlin, Fed. Rep. of Germany

[73] Assignee: Hoechst Aktiengesellschaft, Frankfurt am Main, Fed. Rep. of Germany

[21] Appl. No.: 180,016

[22] Filed: Aug. 21, 1980

[30] Foreign Application Priority Data

Aug. 23, 1979 [DE] Fed. Rep. of Germany ....... 2934069

[51] Int. Cl.³ ............................................. A61K 31/505
[52] U.S. Cl. ..................................... 424/251; 544/287
[58] Field of Search ......................... 424/251; 544/287

[56] References Cited

U.S. PATENT DOCUMENTS 2,694,711 11/1954 Baker et al. ......................... 544/287
3,320,124 5/1967 Waletzky et al. .................... 424/251

OTHER PUBLICATIONS

Joyner, Advances in Pharmacology & Chemistry, vol. 11 (1973), pp. 321, 343 and 344.

*Primary Examiner*—Sam Rosen
*Attorney, Agent, or Firm*—Curtis, Morris & Safford

[57] ABSTRACT

What are disclosed are a method for treating theilerioses, and preparations suitable therefor, with a quinazolinone compound of the formula

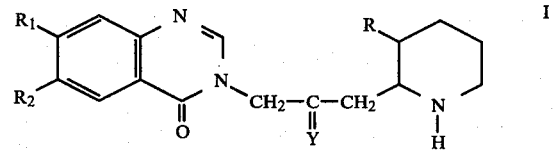

in which $R_1$ and $R_2$, independent of each other, denote halogen such as fluorine, chlorine, bromine or iodine, trifluoromethyl, alkoxy having 1 to 4 carbon atoms, or methyl Y denotes oxygen, sulfur or the oxime group (=N.OH), R denotes hydroxy or acyloxy having 1 to 4 carbon atoms, preferably acetoxy, and X denotes the anion of a physiologically acceptable acid.

3 Claims, No Drawings

PREPARATIONS FOR THE TREATMENT OF THEILERIOSIS AND THEIR USE

U.S. Pat. Nos. 2,694,711 and 3,320,124 relate to quinazolines and to their use for the treatment of malaria and coccidiosis.

It has now been found, surprisingly, that quinazolinones of the formula I:

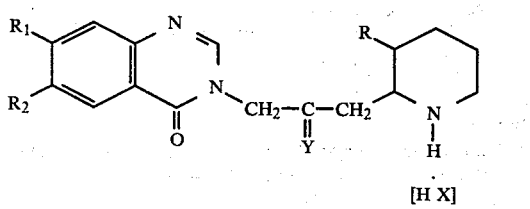

[H X]

in which $R_1$ and $R_2$, independent of each other, denote halogen such as fluorine, chlorine, bromine or iodine, trifluoromethyl, alkoxy having 1 to 4 carbon atoms, or methyl Y denotes oxygen, sulfur or the oxime group (=N.OH), R denotes hydroxy or acyloxy having 1 to 4 carbon atoms, preferably acetoxy, and X denotes the anion of a physiologically acceptable acid are effective against different types of theileria and, therefore, can be used for combatting theileriosis.

Preferred compounds of formula I are those in which $R_1$ and $R_2$, independent of each other, are chlorine, bromine or trifluoromethyl, Y is oxygen, R is hydroxy and X denotes the anion of lactic acid, acetic acid, aceturic acid or hydrobromic acid. 7-Bromo-6-chloro-3-[3-(3-hydroxy-2-piperidyl)-acetonyl]-4-(3H)-quinazolinone lactate is particularly preferred.

The compounds of the formula I can be prepared by the method described in Example 2 of U.S. Pat. No. 2,694,711, optionally with the use of correspondingly substituted quinazolinones, or by the process described in French Patent Specification No. 1,550,956.

The compounds of the formula I are effective especially against theilerioses in animals transmitted by ticks, for example Theileria parva (East Cost fever), Theileria annulata (transcaucasian fever), Theileria lawrencei (corridor disease) and Theileria hirci (malignant theileriosis in sheep and goats).

The compounds of the formula I are, therefore, suitable for the therapy and prophylaxis of the aforesaid theilerioses, for example in cattle, goats and sheep.

The compounds of the formula I can also be used, together with a live vaccine, to produce a preimmunity in the animals treated therewith.

The compounds of the formula I can be administered orally or, if desired, parenterally. For this purpose a salt of a compound of formula I, especially the lactate, dissolved in water or a well tolerated solvent is preferred.

For oral administration, fodder mixtures can be used which contain the compounds of the formula I in an amount from 0.01 to 2% by weight. Tablets, coarse granules, pellets, boles or similar preparations containing from 0.1 to 50% by weight of active substance are also preferred. The active substance is generally blended with one or several conventional pharmaceutical excepients and/or additives. Alternatively, solutions, emulsions or suspensions of the active compound can be administered orally.

For parenteral administration, the compounds of the formula I can be used in the form of solutions of their salts, for example in blood-isotonic solutions, such as glucose or mannitol solution, optionally with the addition of buffers, thickeners, for example cellulose ethers, or polyvinyl pyrrolidone and preservatives.

With one sole administration, a dose of from 0.1 to 3 mg, preferably of from 1 to 2 mg, per kilogram of body weight, calculated on a quinazolone base of the formula I, is used, in the case of oral administration. This dose can also be divided for administration over a period of several days.

To prove the effect against theileriosis, cattle were infected with a multiple of the deadly dose of Theileria annulata or Theileria parva either by infected ticks or by so-called stabilates made from such ticks.

After appearance of the typical symptoms, i.e. fever of 41° C., hard swoolen lymph nodes, distinct aggravation of general state of health, a single dose of 1.2 mg of (±)-trans-7-bromo-6-chloro-3-[3-(3-hydroxy-2-piperidyl)-acetonyl]-4-(3H)-quinazolinone hydrobromide, lactate or aceturate (calculated on the base), was orally administered per kilogram of body weight at the 8th to 10th day (Th. annulata) or 10th to 12th day (Th. parva) after infection. After 2 to 3 days a pronounced improvement of the clinical symptoms and a strong reduction of parasitemia as ascertained by examination of blood smears and biopsy of lymph nodes, could be observed. While control animals died from the infection, there was no mortality with the treated animals. They were, rather, free from fever 3 to 5 days after administration of the drug.

Under otherwise identical conditions, 0.3 mg (calculated on the base) of (±)-trans-7-bromo-6-chloro-3-[3-(3-hydroxy-2-piperidyl)-acetonyl]-4-(3H)-quinazolinone hydrobromide, lactate or aceturate, per kg of body weight, was administered to cattle on the 10th to 13th day after infection. In this case the fever dropped more slowly but about the same reduction of parasitemia was proved by examination of blood smears and biopsy of lymph nodes.

After the treatment, the animals had acquired an immunity that excluded substantially a new outbreak of the disease as could be proved by the examination of blood smears over a prolonged period of time and by reinfections.

EXAMPLE 1,000 Tablets were prepared by mixing 60.86 g of (±)-trans-7-bromo-6-chloro-3-[3-(3-hydroxy-2-piperidyl)acetonyl]-4-(3H)-quinazolinone lactate (corresponding to 50 g of the free base) with 30.14 g of lactose, 45 g of cornstarch, 11 g of highly dispersed silicon dioxide and 3 g of polyethylene glycol 600, and by subsequently granulating the mixture. The granular material was compressed into 1,000 tablets each weighing 150 mg. The tablets were provided with a break score in the center to facilitate a bisection of the dose, for example for the treatment of calves. Prior to administration, the tablets were dissolved in an adequate quantity of water, generally from 2 to 200 ml per tablet.

What is claimed is:

1. A preparation for the treatment of theilerosis comprising an amount, effective against theilerosis, of a quinazolinone compound of the formula:

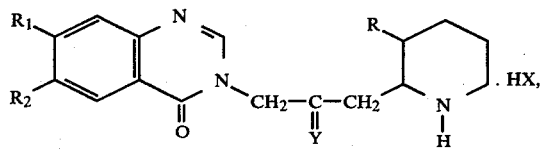

wherein
- R₁ and R₂ independently are halogen, trifluoromethyl alkoxy having 1 to 4 carbon atoms, or methyl,
- Y is oxygen, sulfur, or =OH,
- R is hydroxy or acyloxy having 1 to 4 carbon atoms, and
- X is a lactate, aceturate, or acetate anion, together with a pharmaceutically acceptable carrier therefor.

2. A preparation as in claim 1 wherein said quinazolinone compound is the lactate, aceturate, or acetate of 7-bromo-6-chloro-3-[3-(3-hydroxy-2 piperidyl)-acetonyl]-4-(3H)quinazolinone.

3. A method for combatting theilerosis in animals which comprises administering to said animals an amount, effective against theilerosis, of a quinazolinone compound of the formula

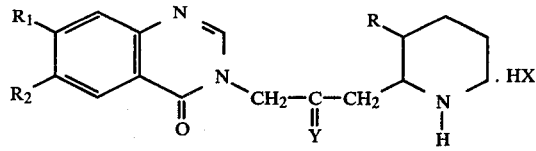

wherein
- R₁ and R₂ independently are halogen, trifluoromethyl alkoxy having 1 to 4 carbon atoms, or methyl,
- Y is oxygen, sulfur, or =NOH,
- R is hydroxy or acyloxy having 1 to 4 carbon atoms, and
- X is an anion of a physiologically acceptable acid.

* * * * *